United States Patent [19]
Sullivan, III et al.

[11] Patent Number: 5,744,024
[45] Date of Patent: Apr. 28, 1998

[54] METHOD OF TREATING SOUR GAS AND LIQUID HYDROCARBON

[75] Inventors: Daniel S. Sullivan, III; Allan R. Thomas, both of Houston; Juan M. Garcia, III, Sugar Land; Paul Yon-Hin, Houston, all of Tex.

[73] Assignee: Nalco/Exxon Energy Chemicals, L.P., Sugar Land, Tex.

[21] Appl. No.: 542,462

[22] Filed: Oct. 12, 1995

[51] Int. Cl.[6] .................................................. C10G 29/20
[52] U.S. Cl. ....................... 208/236; 208/237; 208/207; 423/242.6; 423/242.2
[58] Field of Search ........................ 208/206, 207, 208/236, 237; 423/242.2, 242.6

[56] References Cited

U.S. PATENT DOCUMENTS

| | | | |
|---|---|---|---|
| 3,164,544 | 1/1965 | Bowers | 208/207 |
| 3,884,917 | 5/1975 | Ibbotson | 260/248 |
| 3,915,970 | 10/1975 | Limaye et al. | 260/248 |
| 3,978,137 | 8/1976 | Frame | 208/207 |
| 4,260,479 | 4/1981 | Frame | 208/207 |
| 4,290,913 | 9/1981 | Frame | 208/206 |
| 4,337,147 | 6/1982 | Frame | 208/206 |
| 4,374,104 | 2/1983 | Primack | 423/226 |
| 4,605,737 | 8/1986 | Au | 544/215 |
| 4,631,138 | 12/1986 | Johns et al. | 252/8.555 |
| 4,710,305 | 12/1987 | Allison | 210/747 |
| 4,748,011 | 5/1988 | Baize | 423/228 |
| 4,753,722 | 6/1988 | Le et al. | 208/207 |
| 4,778,609 | 10/1988 | Koch et al. | 252/325 |
| 4,978,512 | 12/1990 | Dillon | 423/226 |
| 5,128,049 | 7/1992 | Gatlin | 210/752 |
| 5,169,411 | 12/1992 | Weers | 44/421 |
| 5,347,004 | 9/1994 | Rivers et al. | 544/180 |
| 5,354,453 | 10/1994 | Bhatia | 208/236 |
| 5,480,860 | 1/1996 | Dillon | 423/228 |

FOREIGN PATENT DOCUMENTS

| | | |
|---|---|---|
| 0438812 | 7/1991 | European Pat. Off. . |
| 4027300 | 3/1992 | Germany . |

*Primary Examiner*—Walter D. Griffin
*Attorney, Agent, or Firm*—Thomas M. Breininger; Kelly L. Cummings; Robert L. Graham

[57] ABSTRACT

Reaction of 1,3,5-tri-substituted-hexahydro-1,3,5-triazine is accelerated in $H_2S$ scavenging by the addition of quaternary ammonium compound. The preferred hexahydro triazines are 1,3,5-tri-methyl-hexahydro-1,3,5-triazines and 1,3,5-tri-methoxypropyl-hexahydro-1,3,5-triazines. The blend of the hexahydro triazine and quaternary ammonium compounds can be used to treat sour gases and liquids (e.g. sour kerosene, crude oil, fuel oils, heating oils, distillate fuels, bunker fuel oil, and the like.

9 Claims, No Drawings

METHOD OF TREATING SOUR GAS AND LIQUID HYDROCARBON

BACKGROUND OF THE INVENTION

This invention relates generally to the treatment of sour gas and liquid hydrocarbon to remove or reduce the levels of hydrogen sulfide therein. In a preferred aspect, the present invention relates to the use of nonregenerative $H_2S$ scavengers in the treatment of hydrocarbon liquids (e.g. kerosene, crude oil, distillate fuels, fuel oil, heating oils, and bunker fuel oils). In another aspect, the invention relates to the treatment of sour gas and oil streams flowing in a flow line. In still another aspect, the invention relates to the use of nonregenerative scavengers to reduce the levels of hydrogen sulfide in natural gas and liquid hydrocarbons during their transportation and storage. In still another aspect, the invention relates to the use of quaternary ammonium compounds to accelerate the scavenging action of $H_2S$ scavengers.

The toxicity of hydrogen sulfide in hydrocarbon streams is well known in the industry and considerable expense and efforts are expended annually to reduce its content to a safe level. Many regulations require pipeline gas to contain no more than 4 ppm hydrogen sulfide.

In large production facilities, it is generally more economical to install a regenerative system for treating sour gas streams. These systems typically employ a compound used in an absorption tower to contact the produced fluids and selectively absorb the hydrogen sulfide and possibly other toxic materials such as carbon dioxide and mercaptans. The absorption compound is then regenerated and reused in the system. Typical hydrogen sulfide absorption materials include alkanolamines, PEG, hindered amines, and the like.

However, during a development stage of a field or in small producing fields where regenerative systems are not economical, it is necessary to treat the sour hydrocarbon production with nonregenerative scavengers.

Based on an article appearing in the *Oil & Gas Journal,* Jan. 30, 1989, nonregenerative scavengers for small plant hydrogen sulfide removal fall into four groups: aldehyde based, metallic oxide based, caustic based, and other processes. In the removal of hydrogen sulfide by nonregenerative compounds, the scavenger reacts with the hydrogen sulfide to form a nontoxic compound or a compound which can be removed from the hydrocarbon. For example, in the formaldehyde type reaction, the reaction produces a chemical complex known as formthionals (e.g., trithiane).

As described in detail below, the present invention employs (a) a nonregenerative triazine scavenger and (b) a compound for accelerating the scavenging action of the scavenger. Aldehyde scavengers of the prior art include low molecular weight aldehydes and ketones and adducts thereof. The low molecular weight aldehydes may also be combined with an alkyl or alkanolamine as disclosed in U.S. Pat. No. 4,748,011. Other aldehyde derived scavengers include the reaction product of low molecular weight alkanolamines and aldehydes disclosed in U.S. Pat. No. 4,978,512. PCT Application WO 92/01481 discloses a method of reducing sulphides in a sewage gas using certain tri-substituted-hexahydro-s-triazines. German reference DE4027300 discloses a regenerative solvent for removing $H_2S$ and mercaptans. U.S. Pat. No. 5,347,004 discloses the use of 1,3,5 alkoxyalkylene hexahydro triazines. Application WO 91 US 5232 discloses hydroxyalkyl triazine scavengers, specifically an N,N',N"-tris(2-hydroxyethyl)hexahydro-s-triazine.

SUMMARY OF THE INVENTION

In accordance with the method of the present invention, sour hydrocarbon fluids such as $H_2S$ sour gas or liquid hydrocarbons are treated with a triazine scavenger composition to reduce the level of $H_2S$ therein. The scavenger composition comprises (a) a 1,3,5-tri-substituted-hexahydro-1,3,5-triazine capable of scavenging $H_2S$ in the fluid, and (b) an effective amount of a quaternary ammonium compound having the following formula:

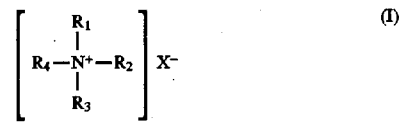

where $R_1$ and $R_2$ are independently alkyl groups or hydroxyalkyl groups having from 1 to 8 carbon atoms;

$R_3$ is an alkyl or aryl group having from 1 to 20 carbon atoms;

$R_4$ is an alkyl or aryl group having from 7 to 20 carbon atoms;

X is an anion selected from chloride and methylsulfate.

It has surprisingly been discovered that the quaternary ammonium compound accelerates the reaction of the triazine scavenger with $H_2S$. The rapid reduction of $H_2S$ in sour hydrocarbons is important in many operations. For example, in the on-loading or offloading of sour hydrocarbons from vessels, the levels of $H_2S$ must be reduced before these operations can commence. The accelerated scavenging of the $H_2S$ in accordance with the present invention can result in huge economic benefits.

The triazine and quaternary ammonium compound can be introduced into the hydrocarbon fluids separately or in a formulation. Each of these compounds can be tailored for oil solubility or water solubility for treating oil or water base fluids.

The weight ratios of the triazine/ammonium quaternary compound may vary with relatively wide ranges. Weight ratios of component (a):(b) in the formulation or direct addition treatment may vary from 10:0.1 to 1:1 for most treatments, with 10:0.05 to 10:1 being preferred.

Although the method of the present invention can employ any of the 1,3,5-substituted- hexahydro-1,3,5-triazine scavengers, the preferred triazines are as follows:

(a) 1,3,5-tri-alkoxyalkyl-hexahydro-1,3,5-triazines (e.g. tri-methoxy propyl (MOPA) triazine);

(b) 1,3,5-tri-alkyl-hexahydro-1,3,5-triazine (e.g. trimethyl triazine); and (c) 1,3,5-tri-alkanol-hexahydro-1,3,5-triazine (e.g. tri-ethanol triazine).

For convenience, the triazine scavengers in some passages herein will be referred to herein as simply triazines or trisubstituted-hexahydro-triazines or other abbreviated names such as MOPA triazine or tri-methyl-triazine. It is to be understood that these shortened names refer to the 1,3,5-trisubstituted-hexahydro-1,3,5-triazines defined above.

As indicated above, the triazine and quaternary compound can be tailored for the treatment desired. For treating oil based fluids, it may be desirable to formulate an oil soluble triazine and an oil soluble quaternary ammonium compound. The MOPA triazines and the trialkyl triazines can be made oil soluble. The ammonium quaternary compound can be oil soluble by selecting the proper R groups: by selecting $R_3$ and/or $R_4$ groups to have relatively long alkyl groups (e.g. $C_{12}$ and above), preferably one of these R groups will be tallow or coco groups.

For water soluble treatments, the triazine may be used in the form as produced—an aqueous solution of the triazine. For water solubility, the $R_3$ and $R_4$ groups of the ammonium compound may contain alkyl or aryl groups containing from 1 to 6 carbon atoms.

The preferred R groups of the quaternary ammonium compound (Formula I) may be as follows:

$R_1$ and $R_2$—alkyl containing 1 to 4 carbon atoms, $R_3$—a benzyl group, $R_4$—a tallow or coco group.

DESCRIPTION OF THE PREFERRED EMBODIMENTS

As mentioned above, the scavenger employed in the method of the present invention comprises two compounds: (a) a 1,3,5-tri-substituted-hexahydro-1,3,5-triazine scavenger, and (b) a quaternary ammonium compound. The description, method of preparation, and use are described in detail below. The hexahydro triazine $H_2S$ scavengers described herein are the preferred compounds for use in the present invention, but it is to be emphasized that this list is not limiting; other hexahydro-triazines may be used—all that is necessary is that the ammonium compound of Formula I accelerates the triazine scavenging reaction.

Substituted Hexahydro-Triazine Scavengers:

The scavenging triazines which are expressly preferred for use in the method of the present invention are:

(1) 1,3,5 tri-alkoxyalkyl-hexahydro-1,3,5-triazines;

(2) 1,3,5 tri-alkyl-hexahydro-1,3,5-triazines;

(3) 1,3,5 tri-alkanol-hexahydro-1,3,5-triazines.

(1.) Alkoxy-Hexahydro Triazines:

The triazines of this group have the following formula:

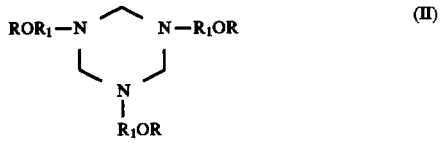

where R is an alkyl group having from 1 to 6 carbon atoms, preferably 1;

$R_1$ is an alkyl group having 2 to 5 carbon atoms, preferably 2 to 3 carbon atoms.

The substituted-hexahydro-triazine of this group may be manufactured by reacting an alkoxyalkyl amine with formalin or a lower aldehyde to form an aqueous solution of the hexahydro-triazine. The water is then distilled off leaving the hexahydro-triazine which can be used in neat form or dissolved in a suitable solvent. Alternatively, the triazine can be used as made (in the aqueous solution). The hexahydro-triazine described above is soluble (up to at least 20% by weight) in a variety of liquids, ranging from water base to oil base. The significance of the solubility is that it can be selectively tailored to treat oil systems with water or oil systems substantially free of water as in refined products.

The preferred hexahydro-triazine is 1,3,5-tri-methoxypropyl-hexahydro-1,3,5-triazine (MOPA hexahydro-triazine).

The MOPA-hexahydro-triazine is prepared by the condensation of methoxypropyl amine (MOPA) with formalin or a lower aldehyde such as formaldehyde. As noted above, the hexahydro-triazine scavenger can be used as manufactured (water solution). For use in oil base formulations, the scavenger can be used in neat form or dissolved in a suitable solvent.

Although the preferred hexahydro-triazine is the MOPA Hexahydro-Triazine, other hexahydro-triazines within the scope of Formula II include 1,3,5-tri-methoxyethyl-hexahydro-1,3,5-triazine (from 2-methoxyethyl amine); 1,3, 5-tri-(3-ethoxypropyl)-hexahydro-1,3,5-triazine (from 3-ethoxypropylamine); 1,3,5-tri-(3-isopropoxypropyl)-hexahydro-1,3,5-triazine(from 3-ethoxypropylamine); 1,3, 5-(3-butoxy-propyl)-hexahydro-1,3,5-triazine (from 3 butoxypropylamine); 1,3,5-tri-(3-butoxypropyl)-hexahydro-1,3,5-triazine (from 3-butoxypropylamine); and 1,3,5-tri-(5-methoxypentyl)-hexahydro-1,3,5-triazine (from 5-methoxypentylamine).

In carrying out the reaction to make the preferred hexahydro-triazine, MOPA is added slowly to a concentrated aqueous solution of formaldehyde and the stoichiometry is maintained so that there is an exact equivalent to a slight excess of the amine at the end of the reaction, maintaining a molar ratio of at least 1.00 to 1.02 moles of the amine to 1.00 moles of formaldehyde for the overall process. Free formaldehyde is minimized to <1000 ppm in the liquid. Slow addition is desirable to control the reaction temperature to below 140° F. For climatization purposes, methanol -or other solvents can be added back without adversely affecting the formaldehyde level. Thus, an essentially quantitative yield of 1,3,5-tri-methoxypropyl-hexahydro-1,3,5-triazine can be formed under conditions which minimize the presence of objectionable amounts of free formaldehyde.

The hexahydro-triazine may also be manufactured by the reverse addition of formaldehyde or paraformaldehyde to the MOPA to produce the same result, provided the temperature is maintained below 140° F. and provided the stoichiometry of the overall process is as described above.

Although the MOPA-hexahydro-triazine can be used as an aqueous solution as produced, it is preferred to distill off the water to produce a neat product, which can be used in that form or mixed with a mutual solvent such as alcohols, ethylene glycol monobutyl ether, or an oil solvent such as heavy aromatic naphthene, alkanes, aromatics, etc. The mutual solvent with the hexahydro-triazine offers the versatility of using the scavenger with either oil or water systems. The concentration of the hexahydro-triazine in the solvent may vary within wide ranges from 5 to 95 wt %, with 25 to 75 wt % being preferred.

The preferred oil solvents are chosen on the basis of the intended application. For example, kerosene and heavy aromatic naphtha offer advantages for carrier solvents to treat oil systems. High boiling process hydrocarbon solvents offer advantage as a carrier to treat higher temperature asphalt materials.

(2.) Alkyl Hexahydro-Triazines:

The triazines of this group have the following formula:

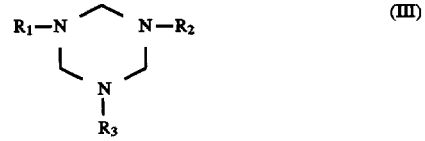

where $R_1$, $R_2$, and $R_3$ may be the same or different and are each alkyl groups having from 1 to 4 carbon atoms.

The preferred alkyl hexahydro triazine is 1,3,5-trimethyl-hexahydro-1,3,5-triazine.

The 1,3,5-trimethyl-hexahydro-1,3,5-triazine may be prepared by the condensation reaction of a trimethylamine and formaldehyde.

The formaldehyde may be in the form of formalin or paraformaldehyde, with the former being preferred.

Other compounds such as solvents may be present in the final product.

In carrying out the reaction, an aqueous solution of methylamine is added slowly to a concentrated aqueous methanol-free solution of formaldehyde and the stoichiometry is maintained so that there is a slight excess of methylamine at the end of the reaction, maintaining a molar ratio of at least 1.01 (e.g. about 1.02 moles) of methylamine to 1.00 moles of formaldehyde for the overall process. Free formaldehyde is minimized to <1000 ppm in the liquid. Slow addition is desirable to control the reaction temperature to below 140° F. For climatization purposes, methanol or other solvents can be added back without adversely affecting the formaldehyde level. Thus, an essentially quantitative yield of 1,3,5-trimethyl-hexahydro-1,3,5-triazine can be formed under conditions which minimize the presence of objectionable amounts of free formaldehyde.

The triazine may also be manufactured by the reverse addition of formaldehyde to methylamine to produce the same result, provided the temperature is maintained below 105° F. to minimize methylamine loss by evaporation and provided the stoichiometry of the overall process is as described above.

(3.) Hydroxyalkyl Hexahydro Triazines:

The triazines of this group have the following formula:

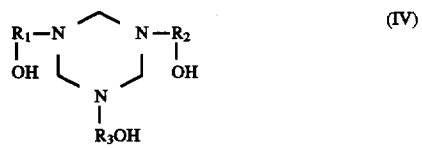

(IV)

where $R_1$, $R_2$, and $R_3$ are the same or different and are alkyl groups containing from 1 to 6 carbon atoms.

These triazines may be prepared by the reaction of an alkanol amine (having from 1 to 6 carbon atoms) and an aldehyde, preferably formaldehyde in a molar ratio of 1:0.25 to 1:10. The reaction is described in detail in U.S. Pat. No. 4,978,512, the disclosure of which is incorporated herein by reference.

The preferred triazine of this group is 1,3,5-tri-(2-hexahydroethyl)-hexahydro-S-triazine.

Quaternary Ammonium Compound:

The quaternary ammonium compounds of Formula I include benzyl cocoalkyl dimethyl quaternary ammonium chloride, dicocodimethylammonium chloride, ditallowdimethylammonium chloride, di(hydrogenated tallow alkyl) dimethyl quaternary ammonium methyl chloride, methyl bis (2-hydroxyethyl) cocoalkyl quaternary ammonium chloride, dimethyl(2-ethyl) tallow ammonium methyl sulfate, and hydrogenated tallow alkyl (2-ethylhexyl) dimethyl quaternary ammonium methylsulfates. Most of these quaternary ammonium compounds are commercially available. (See Experiments.) Formula I can be tailored to make it oil soluble or water soluble.

Operations:

Although the two components (triazine and quaternary ammonium compound) can be separately injected into the system being treated, it is preferred to prepare a formulation of the two components and inject the formulation into the system.

The formulation may be as follows:

|  | Wt % of Formulation | |
|---|---|---|
|  | Range | Preferred Range |
| Solvent | 0 to 78 | 0 to 47 |
| Triazine | 20 to 98 | 50 to 95 |
| Quaternary Ammonium Compound | 2 to 20 | 3 to 10 |

For oil base formulations, suitable solvents include the aliphatic and aromatic solvents. For water base formulations, solvents include water, alcohol, glycol, mutual solvents, and blends thereof.

In carrying out the method of the present invention, the scavenging formulation is added to the gas or oil stream in a concentration sufficient to substantially reduce the levels of $H_2S$ therein. In gas, generally, generally from 0.01 to 0.12, preferably from 0.02 to 0.10, most preferably from 0.04 to 0.08 gallons of the triazine scavenger per MMSCF for each ppm of $H_2S$ removed will be sufficient for most applications. The treatment may also be based on weight of $H_2S$ in the gas. From 1 to 50, preferably 2 to 20 pounds of triazine per pound of $H_2S$ removed will normally be required in oil and gas streams. Typically, from 50 to 3000 ppm of the scavenger in the stream will be used, preferably 1000 ppm or less.

In treating hydrocarbon streams, the scavenging formulation contained in a solvent, such as water or alcohol or mutual solvent or aromatic solvent, may be injected by conventional means such as a chemical injection pump or any other mechanical means for dispersing chemicals in the stream. The injection may be in the flow lines or circulation lines or the gas may be passed through an absorption tower containing a solution of the triazine.

In addition to the components described above, the chemical formulations may also contain other compounds such as ethoxylated alcohols, ethoxylated phenols, sulfates of ethoxylated alcohols and phenols, amine dispersants, corrosion inhibitors, and the like.

The $H_2S$ scavenging ability of the 1,3,5-tri-substituted hexahydro-1,3,5-triazine is believed to be due to its reaction with hydrogen sulfide to produce sulfur containing organic compounds such as dithiazines. The quaternary ammonium compound catalyzes or accelerates this reaction.

Experiments:

Series I Tests:

Preparation of the Triazines:

The MOPA-hexahydro-triazine scavenger used in the experiments was prepared as follows:

A stainless steel 1-liter reactor was charged with 476.56 gr. of formalin solution (37% active formaldehyde) and 523.44 gr. of methoxypropylamine was slowly added over a period of about 15 minutes. The reaction exotherm was controlled with an ice bath. The reaction temperature was maintained between 56° C. to 68° C. When methoxypropylamine was complete, the reaction mixture was heated to remove water and methanol (from formalin) by distillation. The distillation was terminated as the reaction mixture approached 150° C. The reactor contents were then rapidly cooled to room temperature. A yield of 582 grams (Sample I-A) and 583 grams (Sample I-B) of triazine was obtained. Sample I-A was clear pale yellow and Sample I-B was light in color. Subsequent preparations have established that the preferred reaction temperature is 50° C. to 60° C. and that the preferred cutoff temperature for the distillation is a pot temperature of 130° C.

The trimethyl triazine was prepared as described under the section headed "Alkyl-Hexahydro-Triazines" above.

The Quaternary Ammonium Compounds:

Benzylcocodimethyl quaternary ammonium chloride was used in Sample I-E. This compound is marketed by AKZO Nobel Chemicals, Inc. as Arquad 2HT-75.

Soya quat ethoxylated was used in Sample I-F.

Test Procedure:

Each hydrogen sulfide scavenging test was conducted by saturating kerosene (1 quart) with $H_2S$ gas at room temperature. The scavenger was added to the kerosene and shaken for 5 minutes. The concentration of the $H_2S$ in the vapor phase was determined at frequent intervals.

The samples tested were as follows:

| Sample | Concentration of Scavenger or Blend (ppm) |
|---|---|
| Blank - no scavenger | 0 |
| I-A - MOPA triazine | 2000 |
| I-B - MOPA triazine | 2000 |
| I-C - | 2000 |
| 80% MOPA triazine | |
| 20% NEO Acid[1] | |
| I-D - | 2000 |
| 80% MOPA triazine | |
| 20% Ethoxylated nonyl phenol (10 moles) | |
| I-E - | 2000 |
| 80% MOPA triazine | |
| 20% Benzylcocodimethyl Ammonium Chloride | |
| I-F - | 2000 |
| 80% MOPA triazine | |
| 20% Soya quaternary ethoxylated | |

[1]NEO Acid is a hindered carboxylic acid marketed by Exxon Chemical Company.

The samples representing the present invention were Samples I-E and I-F.

The Series I Test results are presented in Table I.

TABLE I

| Sample | Scavenger | Elapsed Time (Hours): | $H_2S$ Concentration (wt %) in Vapor Phase | | | |
|---|---|---|---|---|---|---|
| | | | 0 | 1.5 | 16.75 | 24 |
| Blank | | | 1.10 | 1.10 | 1.10 | 1.00 |
| I-A | MOPA triazine | | 1.10 | 1.04 | 0.35 | 0.13 |
| I-B | MOPA triazine | | 1.10 | 1.05 | 0.35 | 0.13 |
| I-C | MOPA triazine NEO Acid | | 1.10 | 1.05 | 0.40 | 0.17 |
| I-D | MOPA triazine Ethoxylated nonylphenol | | 1.10 | 1.08 | 0.39 | 0.14 |
| I-E | MOPA triazine Benzylcocodimethyl ammonium chloride | | 1.10 | 1.05 | 0.13 | 0.01 |
| I-F | MOPA triazine Soya quat. ethoxylated | | 1.10 | 1.00 | 0.13 | 0.01 |

The tests were carried out for an additional 2½ days at which time all of the samples containing a scavenger or scavenger blend tested zero $H_2S$ in the vapor phase. However, the data demonstrate the acceleration of the quaternary ammonium compound on scavenging ability of the triazines. The two samples (I-E and I-F) containing a blend of the MOPA triazine and the quaternary ammonium compound tested substantially zero $H_2S$ in the vapor phase after 24 hours, but the other samples (with scavenger) had an average of about 0.14% $H_2S$ in the vapor phase after 24 hours.

Series II Tests:

Additional vapor phase tests were carried out using a solvent (Mentor 28, a kerosene) substantially saturated with $H_2S$ at room temperature.

The samples tested were as follows:

tri-methyl-hexahydro triazine solution (34.4 wt % triazine in water; referred to as Triazine in TABLE II);

N-benzyl dimethyl cocoamine ($C_{12}$–$C_{18}$) quaternary salt containing 15.5% isopropanol and 1.1% water (referred to as Quat in TABLE II).

The data for the SERIES II Tests are presented in TABLE II.

TABLE II

| Sample No. | Treatment | Treatment Concentration (ppm) | Time (Hrs.): | $H_2S$ Concentration (ppm) in Vapor Phase | | |
|---|---|---|---|---|---|---|
| | | | | 2 | 6 | 26 |
| Blank | 0 | 0 | | 60,000 | 45,000 | 56,000 |
| II-B | Triazine | 1200 | | 56,000 | 44,600 | 36,600 |
| II-C | Triazine | 2400 | | 49,000 | 32,600 | 3,280 |
| II-D | Triazine | 4800 | | 36,000 | 18,100 | 200 |
| II-E | 95% Triazine 5% Quat. | 1200 | | 45,000 | 31,600 | 19,100 |
| II-F | 95% Triazine 5% Quat. | 2400 | | 39,600 | 14,700 | 520 |
| II-G | 95% Triazine 5% Quat. | 4800 | | 12,800 | 11 | 1 |
| II-H | 90% Triazine 10% Quat. | 1200 | | 47,700 | 34,800 | 21,600 |
| II-I | 90% Triazine 10% Quat. | 2400 | | 41,200 | 15,100 | 550 |
| II-J | 90% Triazine 10% Quat. | 4800 | | 14,400 | 10 | 1 |
| II-K | 80% Triazine 20% Quat. | 1200 | | 47,000 | 34,800 | 21,500 |
| II-L | 80% Triazine 20% Quat. | 2400 | | 43,800 | 17,500 | 500 |
| I-M | 80% Triazine | 4800 | | 23,200 | 230 | 4 |

Series III Tests:

Vapor tests were conducted using sour crude naphtha at room temperature using the same 1,3,5-tri-methyl-hexahydro-1,3,5-triazine and quaternary ammonium compound in Series II Tests. The Test data were as follows:

| Sample No. | Treatment | Treatment Concentration (ppm) | Vapor Phase $H_2S$ (ppm) Time (Hrs.): 12 Hrs. |
|---|---|---|---|
| Blank | 0 | 0 | 5,600 |
| III-A | Triazine | 500 | 63 |
| III-B | Triazine | 1,000 | 5 |
| III-C | 95% Triazine 5% Quat. | 500 | 0 |
| III-D | 95% Triazine 5% Quat. | 1,000 | 0 |

Series IV Tests:

Additional bottle tests were run using the 1,3,5-trimethyl-hexahydro-1,3,5-triazine and quaternary ammonium compound of Series II Tests, except these tests were carried out at about 154° F. The hydrocarbon was kerosene substantially saturated with $H_2S$. The test results are shown in TABLE IV.

TABLE IV

| Sample No. | Treatment | Treatment Concentration (ppm) | Time (Hrs.): | $H_2S$ in Vapor Phase (ppm) | | |
|---|---|---|---|---|---|---|
| | | | | 2 | 6 | 26 |
| Blank | 0 | 0 | | 68,000 | 60,000 | 57,000 |
| IV-A | Triazine | 1200 | | 44,000 | 32,600 | 3,720 |
| IV-B | Triazine | 2400 | | 31,000 | 3,000 | 23 |
| IV-C | Triazine | 4800 | | 3,800 | 54 | 17 |
| IV-D | 95% Triazine 5% Quat. | 1200 | | 35,600 | 21,800 | 9,500 |
| IV-E | 95% Triazine 5% Quat. | 2400 | | 8,300 | 930 | 43 |
| IV-F | 95% Triazine 5% Quat. | 4800 | | 70 | 38 | 18 |
| IV-G | 90% Triazine 10% Quat. | 1200 | | 35,500 | 20,500 | 5.700 |
| IV-H | 90% Triazine 10% Quat. | 2400 | | 7,700 | 1,280 | 51 |
| IV-I | 90% Triazine 10% Quat. | 4800 | | 68 | 1.34 | 2.4 |
| IV-J | 80% Triazine 20% Quat. | 1200 | | 35,300 | 21,200 | 660 |
| IV-K | 80% Triazine 20 Quat. | 2400 | | 10,700 | 1,460 | 69 |
| IV-L | 80% Triazine 20% Quat. | 4800 | | 94 | 92 | 27 |

Series V Tests:

Additional bottle tests were carried out using kerosene with lower levels of $H_2S$ and at room temperature (approximately 65° F.). The 1,3,5-tri-methyl-hexahydro-1,3,5-triazine and the quaternary ammonium compounds were the same as used in Series II Tests. The test date are presented in TABLE V.

TABLE V

| Sample No. | Treatment | Treatment Concentration (ppm) | Time (Hrs.): | $H_2S$ in Vapor Phase (ppm) | | |
|---|---|---|---|---|---|---|
| | | | | 2-½ | 5 | 19 |
| Blank | 0 | 0 | | 10,400 | 9,400 | 10,000 |
| V-A | Triazine | 500 | | 8,800 | 6,600 | 2,900 |
| V-B | Triazine | 500 | | 8,900 | 6,700 | 2,900 |
| V-C | 95% Triazine 5% Quat. | 500 | | 6,220 | 2,660 | 0 |
| V-D | 90% Triazine 10% Quat. | 500 | | 5,400 | 2,000 | 0 |

TABLE V-continued

| Sample No. | Treatment | Treatment Concentration (ppm) | Time (Hrs.): | H₂S in Vapor Phase (ppm) | | |
|---|---|---|---|---|---|---|
| | | | | 2-½ | 5 | 19 |
| V-E | 80% Triazine 20% Quat. | 500 | | 5,600 | 1,480 | 0 |

Series VI Tests:

Additional tests were carried out to determine the effectiveness of blends of 1,3,5-tri-methyl-hexahydro-1,3,5-triazine and various quaternary ammonium compounds.

Test Procedure: Hydrogen sulfide vapor headspace concentrations in sour No. 6 Fuel Oil are reliably determined using the can test method. The method requires filling a one liter metal can with 500 mL of No. 6 Fuel Oil, shaking the sample can to release additional H₂S trapped in the bulk fluid, and heating the samples to 140° F. in a water bath for a predetermined amount of time (e.g. 1 hour). After about 12 hours (overnight), hydrogen sulfide concentrations are determined using Drager H₂S detector tubes. The sour hydrocarbon used in these samples was No. 6 Fuel Oil containing relatively low levels of H₂S (about 400 ppm max.).

| Samples | | Wt % |
|---|---|---|
| VI-A | • tri-methyl-hexahydro-triazine[1] | 100 |
| VI-B | • tri-methyl-hexahydro-triazine[1] | 95 |
| | • methyl bis(2-hydroxyethyl)cocoalkyl quaternary ammonium chloride[2] | 5 |
| VI-C | • tri-methyl-hexahydro-triazine[1] | 95 |
| | • hydrogenated tallow (2-ethylhexyl) dimethyl quaternary ammonium chloride methosulfate[3] | 5 |
| VI-D | • trimethyl-hexahydro-triazine[1] | 95 |
| | • benzyl cocoalkyl dimethyl quaternary ammonium chloride[4] | 5 |
| VI-E | • trimethyl-hexahydro-triazine[1] | 95 |
| | • dimethyl di(cocoalkyl) quaternary ammonium chloride[5] | 5 |

[1]34.4 wt % solution in water
[2]marketed by AKZO Chemicals, Inc. as ETHOQUAD C/12
[3]marketed by AKZO Chemicals, Inc. as ARQUAD HTL 8-MS
[4]marketed by AKZO Chemicals, Inc. as ARQUAD DMCB-80
[5]marketed by AKZO Chemicals, Inc. as ARQUAD 2 C-75

The vapor phase test results carried out at 140° F. are presented in TABLE VI.

TABLE VI

| Sample No. | Treatment Concentration (ppm) | Time (Hrs.): | H₂S Vapor Phase (ppm) | | | | |
|---|---|---|---|---|---|---|---|
| | | | 1 | 2 | 3 | 4 | 20 |
| Blank | 0 | | 275 | 475 | 425 | 400 | 380 |
| VI-A | 100 | | 400 | 390 | 355 | 325 | 120 |
| VI-B | 100 | | 325 | 390 | 400 | 300 | 120 |
| VI-C | 100 | | 390 | 280 | 260 | 240 | 110 |
| VI-D | 100 | | 450 | 365 | 240 | 290 | 135 |

Series VII Tests

Additional tests were carried out to determine the effectiveness of blends of MOPA-hexahydro-triazine in the treatment of hydrotreated heavy naphtha.

Test Procedure: One gallon samples of hydrotreated heavy naphtha were sparged with H2S for 30–60 seconds. Preparation of individual samples involved transferring 500 mL of sour naphtha into quart size, metal containers. After filling, each sample can was immediately capped. The samples were shaken, then placed in a hot water bath and held at 105° F. for 20 and 30 minute heating cycles.

At the end of each heating cycle, samples were removed from the hot water bath and shaken to release additional H₂S into the vapor headspace of each sample can. Drager tubes measured initial H₂S vapor headspace concentrations before treatment.

Loss of H₂S was avoided by inserting the Drager tube through a No. 8 rubber stopper. The rubber stopper-Drager tube assembly quickly replaced each metal cap before measuring the H₂S content.

Once initial H₂S concentrations were determined, samples were dosed with an appropriate amount of H₂S scavenger. After dosing, samples were shaken to ensure thorough mixing and reimmersed into the hot water bath for the designated heating cycle. Dosed samples were left heating overnight and a final vapor headspace concentration was determined the following day. Measurements taken determined the rate of H₂S reduction over time.

Samples

The samples used in these tests were as follows:

| VII-A | 1,3,5-tri-methoxypropyl-hexahydro-1,3,5-triazine (99% and 0.2% water) |
|---|---|
| VII-B | Sample VIIA - 60 wt % Aromatic Solvent - 40 wt % |
| VII-C | Sample VII-A - 60 wt % Benzyl cocoalkyl dimethyl quaternary ammonium chloride[1] - 5 wt % Aromatic solvent - 35 wt % |
| VII-D | Sample VII-A - 60 wt % Hydrogenated tallow alkyl (2-ethylhexyl) dimethyl quaternary ammonium sulfate[2] - 5 wt % Aromatic solvent - 35 wt % |
| VII-E | Sample VII-A - 60 wt % Dimethyl di(cocoalkyl) Quaternary amonium chloride[3] - 5 wt % Aromatic solvent- 35 wt % |

[1]marketed by AKZO Chemicals, Inc. as ETHOQUAD C/12
[2]marketed by AKZO Chemicals, Inc. as ARQUAD HTL-MS
[3]marketed by AKZO Chemicals, Inc. as ARQUAD 2C-75

The Series VII Test results are shown in Table VII.

TABLE VII

| Sample No. | Treatment Concentration | Time (Hrs.): | H₂S in Vapor Phase (ppm) | | | |
|---|---|---|---|---|---|---|
| | | | 0.5 | 1 | 2 | 21 |
| Blank | 0 | | 825 | 915 | 840 | 750 |
| VII-B | 175 | | 1060 | 1130 | 950 | 500 |
| VII-C | 175 | | 1060 | 935 | 766 | 520 |
| VII-D | 175 | | 1090 | 870 | 835 | 475 |
| VII-E | 175 | | 1025 | 800 | 750 | 410 |

Series VIII Tests

Additional vapor phase tests were conducted similar to the SERIES VI TESTS using trimethyl-hexahydro-triazine in the treatment of heavy naphtha. The Test procedure was the same as described in the SERIES VII TESTS and the scavenger samples used in the naphtha were the same as identified in the SERIES VI TESTS. The test results are presented in TABLE VIII.

TABLE VIII

| Sample No. | Treatment Concentration (ppm) | Time (Min.): | H₂S Vapor Phase (ppm) | | |
|---|---|---|---|---|---|
| | | | 20 | 60 | 80 |
| Blank | 0 | | 190 | 140 | 140 |
| VI-A | 50 | | 275 | 100 | 50 |
| VI-B | 50 | | 225 | 50 | 15 |
| VI-C | 50 | | 265 | 75 | 50 |
| VI-D | 50 | | 325 | 70 | 15 |
| VI-E | 50 | | 225 | 115 | 80 |

At 20 hours of elapsed time, all samples with scavenger tested zero H₂S in the vapor phase.

Summary of Test Results:

The following summarizes the tests:

The SERIES I TESTS with MOPA-Triazine and two separate quaternary ammonium compounds demonstrate the effectiveness of this blend over the MOPA Triazine alone or with other additives. The results with Samples I-E and I-F of the blend reduced the vapor phase H₂S to 0.13% in 16.75 hours whereas the triazine alone or with other additives reduced the H₂S in the vapor phase to about 0.40%. Moreover, at 24 hours the H₂S had been substantially scavenged in Samples I-E and I-F but not in Samples I-A, I-B, I-C, and I-D.

The SERIES II TESTS demonstrate the effectiveness of the tri-methyl triazine at various ratios with the quaternary ammonium compound and various concentrations of the formulations. Note that these tests were carried out at near H₂S saturation of Kerosene (e.g. 60,000 ppm).

Because of the high concentration of the H₂S in the samples, large treatment dosages were required to effect H₂S scavenging. At comparable dosage treatments, the Triazine/Quat blend accelerated scavenging in all ratios tested. The most dramatic results were obtained at treatment rates of 2,400 ppm and above. Even at the 1,200 ppm treatments, however, the Triazine/Quat blend gave much better performance than the triazine alone.

The SERIES III TESTS demonstrate the effect of the Triazine/Quat blend on sour crude naphtha. Using the triazine alone the H₂S in the vapor phase was not completely scavenged, but with the blend, no H₂S remained in the vapor phase after 12 hours.

The SERIES IV TESTS were the same as the SERIES II TESTS except that these tests were carried out at a higher temperature (room temperature vs. 154° F.). With respect to the higher treatment dosages (i.e. 2,400 and 4,800 ppm), the SERIES IV TEST results were about the same as the SERIES II TEST results. The blend greatly accelerated the scavenging activity. (Compare the 6 hour results at comparable treatment dosages.)

The SERIES V TESTS compared the performance of the Triazine/Quat (at various ratios) blend with Triazine alone at 500 ppm and at 140° F. and in fuel oil No. 6. Here again, the blend in all weight ratios accelerated scavenging.

The SERIES VI TESTS demonstrate a problem associated with many heavy hydrocarbons such as fuel oil and heavier. With time and under high temperature, H₂S measured actually increased. The high viscosity of the heavy hydrocarbons may have delayed or retarded the samples reaching equilibrium. See for example the test results of the blank in TABLE VI: H₂S at one hour was 275 ppm but increased to 475 after 2 hours. The unpredictable behavior of sour hydrocarbons makes them extremely difficult to treat. Nevertheless, two of the three Triazine/Quat blends (Samples VI-C and VI-D) accelerated scavenging at low weight ratio of the Quat and at low ppm treatment.

The SERIES VII TESTS demonstrate that MOPA Triazine with the quat. accelerated scavenging in heavy naphtha. Compare 2-hour data for Sample VII-B (naphtha with triazine) with Samples VII-C and VII-E (naphtha with triazine and quat.).

The SERIES VIII TESTS demonstrate the acceleration of the quaternary ammonium compound on the scavenging action of trimethyl-hexahydro triazine in the treatment of heavy naphtha. Compare Samples VI-B and VI-D (triazine/Quat blend) with Sample VI-A (triazene alone) at the elapsed time of 80 minutes.

Summary of All of the Experiments:

The data generated in Experiments SERIES I through SERIES VIII TESTS demonstrate the accelerating effects of the scavenging rate of the Triazines in the treatment of a variety of hydro-carbons under a variety of conditions, and at various treatment ratios and concentrations.

The acceleration of the scavenging reaction is important because many of the triazines, particularly those used in hydrocarbon liquids, are very slow reacting with H₂S which limits their utility in many treatments. The reaction acceleration in accordance with the present invention renders the slow reacting triazines highly useful, particularly in heavy oils.

What is claimed is:

1. A method of reducing H₂S in a hydrocarbon fluid which comprises contacting the fluid with an effective amount of a scavenging composition, comprising an aqueous solution of
   (a) a 1,3,5-trimethyl-hexahydro-1,3,5 triazine H₂S scavenger; and
   (b) a quaternary ammonium compound having the following formula:

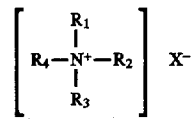

where $R_1$ and $R_2$ are independently alkyl groups or hydroxyalkyl groups having from 1 to 4 carbon atoms
$R_3$ is a benzyl group, and
$R_4$ is an alkyl or aryl group having from 7 to 20 carbon atoms, and
$X^-$ is an anion selected from the group consisting of chloride and methyl sulfate;
wherein the amount of the quaternary ammonium compound is sufficient to accelerate the H₂S scavenging action of the 1,3,5-trimethyl-hexahydro-1,3,5 triazine in comparison with the scavenging action of said triazine without the quaternary ammonium compound.

2. The method of claim 1 wherein the weight ratio of (a):(b) ranges from 10:0.1 to 1:1.

3. The method of claim 1 wherein $R_4$ is a tallow or coco group.

4. The method of claim 1 wherein the hydrocarbon fluid is a hydrocarbon liquid.

5. The method of claim 4 wherein the hydrocarbon liquid is an oil selected from kerosene, crude oil, fuel oils, heating oils, distillate fuels, and bunker fuel oil.

6. A method of reducing H₂S in a hydrocarbon fluid comprising introducing into the fluid from 50 to 3,000 ppm by volume of a scavenging composition comprising (a) a 1,3,5-trimethylhexahydro-1,3,5-triazine, and (b) a water soluble quaternary ammonium compound which accelerates the scavenging effect of the triazine scavenger, the weight ratio of (a):(b) in the scavenging composition being between 10:0.1 to 1:1.

7. The method of claim 6 wherein components (a) and (b) are introduced into the fluid in a weight ratio ranging from 10:0.5 to 10:1.

8. The method of claim 6 wherein the hexahydro triazine and the quaternary ammonium compound are introduced into the fluid as an aqueous solution.

9. The method of claim 6 wherein the quaternary ammonium compound is benzyl cocalkyl dimethyl quaternary ammonium chloride.

* * * * *